United States Patent
Birks et al.

(10) Patent No.: US 11,614,384 B2
(45) Date of Patent: Mar. 28, 2023

(54) ENCLOSURE FOR MOBILE MONITORING OF THE COMPOSITION AND PROPERTIES OF AMBIENT AIR

(71) Applicant: Ludlum Measurements, Inc., Sweetwater, TX (US)

(72) Inventors: John William Birks, Longmont, CO (US); Peter Christian Andersen, Superior, CO (US); Craig Joseph Williford, Golden, CO (US); Andrew Allen Turnipseed, Arvada, CO (US)

(73) Assignee: LUDLUM MEASUREMENTS, INC., Sweetwater, TX (US)

( * ) Notice: Subject to any disclaimer, the term of this patent is extended or adjusted under 35 U.S.C. 154(b) by 425 days.

(21) Appl. No.: 17/062,575

(22) Filed: Oct. 3, 2020

(65) Prior Publication Data

US 2021/0101437 A1    Apr. 8, 2021

Related U.S. Application Data

(60) Provisional application No. 62/909,994, filed on Oct. 3, 2019.

(51) Int. Cl.
*G01N 1/22* (2006.01)
*G01N 33/00* (2006.01)

(52) U.S. Cl.
CPC ....... *G01N 1/2273* (2013.01); *G01N 33/0009* (2013.01); *Y02A 50/20* (2018.01)

(58) Field of Classification Search
CPC ... G01N 1/2273; G01N 33/0009; Y02A 50/20
See application file for complete search history.

(56) References Cited

U.S. PATENT DOCUMENTS

2011/0257922 A1* 10/2011 Fang .................... G01N 1/2273
702/45
2013/0047704 A1* 2/2013 Bae ...................... G01N 1/2273
73/31.02

FOREIGN PATENT DOCUMENTS

KR    20110131787 A  * 12/2011  ............. G06Q 50/26

OTHER PUBLICATIONS

English translation of KR20110131787 accessed from iq.ip.com Jan. 24, 2023.*

(Continued)

*Primary Examiner* — David Z Huang
*Assistant Examiner* — Jean F Morello
(74) *Attorney, Agent, or Firm* — Polson Intellectual Property Law, PC; Margaret Polson; Christopher Sylvain

(57) ABSTRACT

An enclosure or housing for an air monitoring instrument package for mounting on the roof or other surface on the outside of vehicles such as cars, trucks, buses, trams, trains and ships. By measuring air pollutants from moving vehicles, it is possible to explore the distribution of air pollutants throughout a city or rural area for the identification of sources of different pollutants, estimating human exposures to air pollutants, and mapping air pollutants with high resolution. The disclosed device provides continuous sampling of outside air while simultaneously protecting the delicate instruments from weather elements such as high wind, rain, snow, sleet and hail. The design also allows a nearly constant flow rate of sampled air independent of vehicle velocity. An optional impaction region further reduces transmission of mist and large particles to the chamber containing the measurement package.

21 Claims, 2 Drawing Sheets

(56) References Cited

OTHER PUBLICATIONS

American Lung Association, "State of the Air" Report 2019. 167 pages.

Apte et al, "High-Resolution Air Pollution Mapping with Google Street View Cars: Exploiting Big Data", Environmental Science & Technology (a publication of the American Chemical Society), vol. 51 (2017, pp. 6999-7008, published Jun. 5, 2017. 10pages.

Cross et al, "Use of electrochemical sensors for measurement of air pollution: correcting interference response and validating measurements", Atmospheric Measurement Techniques (Copernicus Publications/European Geosciences Union), vol. 10, pp. 3575-3588, Sep. 29, 2017. 14 pages.

Ellenburg et al, "Global Ozone (GO3) Project and AQTreks: Use of evolving technologies by students and citizen cientists ro monitor air pollutants", Atmospheric Environment (published by Elsiever Ltd ), online publication Sep. 27, 2019. 16 pages.

Feinberg et al, "Long-term evaluation of air sensor technology under ambient conditions in Denver, Coorado", Atmospheric Measurement Techniques (Copernicus Publications/European Geosciences Union), vol. 11, pp. 4605-4615, Aug. 8, 2018. 11 pages.

Hagan et al, "Calibration and assessment of electrochemical air quality sensors by co-location with regulatory-grade instruments", Atmospheric Measurement Techniques (Copernicus Publications/European Geosciences Union), vol. 11, pp. 315-328, Jan. 15, 2018. 15 pages.

Jiao et al, "Community Air Sensor Network (CAIRSENSE) project: evaluation of low-cost sensor performance in a suburban environment in the southeastern United States", Atmospheric Measurement Techniques (Copernicus Publications/European Geosciences Union), vol. 9, pp. 5281-5292, Nov. 1, 2016. 12 pages.

Malings et al, "Fine particle mass monitoring with low-cost sensors: Corrections and ling-term performance evaluation", Aerosol Science and Technology online journal, Jun. 10, 2019. 16 pages.

Mijling et al, "Field calibration of electrochemical NO2 sensors in a citizen science context", Atmospheric Measurement Techniques (Copernicus Publications/European Geosciences Union), vol. 11, pp. 1297-1312, Mar. 5, 2018. 16 pages.

Piedrahita et al., "The next generation of low-cost personal air quality sensors for quantitative exposure monitoring", Atmospheric Measurement Techniques (Copernicus Publications/European Geosciences Union), vol. 7, pp. 3325-3336 Oct. 7, 2014. 12 pages.

Rai et al, "End-user perspective of low-cost sensors for outdoor air pollution monitoring", Science of the Total Environment (published by Elsiever Ltd.), online publication Jul. 27, 2017. 15 pages.

Steinle et al., "Quantifying human exposure to air pollution—Moving from static monitoring to spatio-temporally resolved personal exposure assessment", Science of the Total Environment (published by Elsiever Ltd.), online publication Nov. 25, 2012. 10 pages.

Zimmerman et al., "A machine learning calibration model using random forests to improve sensor performance for lower-cost air quality monitoring", 11 Atmospheric Measurement Techniques (Copernicus Publications/European Geosciences Union), vol. 11, pp. 291-313, Jan. 15, 2018. 23 pages.

Health Effects Institute, "State of Global Air 2019", Special Report, 2019, Health Effects Institute, Boston, MA, ISSN 2578-6873 [24 pages].

\* cited by examiner

ENCLOSURE FOR MOBILE MONITORING OF THE COMPOSITION AND PROPERTIES OF AMBIENT AIR

BACKGROUND

Currently, air pollutants are monitored in the U.S. by state and local government agencies at a few fixed monitoring stations scattered throughout cities and rural areas and located with the goal of providing average concentrations of air pollutants for determining compliance with National Ambient Air Quality Standards (NAAQS) set by the U.S. Environmental Protection Agency (US-EPA). These stations contain highly accurate instruments that are maintained and calibrated in accordance with procedures established by the US-EPA. Unfortunately, however, the EPA-mandated monitoring stations provide very limited information about the distribution of air pollutants within a city or region and what actual individual exposures are. Estimates of human exposure are especially important because of the severe health effects of air pollutants (Steinle et al., 2013). According to the American Lung Association's *State of the Air* 2019 report (American Lung Association, 2019), during the period 2014-2016, 141 million Americans, or about 43% of the U.S. population, lived in counties that had unhealthy levels of air pollutants. The World Health Organization (WHO) has estimated that ambient air pollution currently causes 4.2 million premature deaths worldwide each year, primarily as a result of increased mortality from stroke, heart disease, asthma, COPD, lung cancer and acute respiratory infections, with more than 90% of people living in areas exceeding the WHO Guidelines for healthy air. After smoking, high blood pressure and poor diet, air pollution is the fourth-highest cause of death worldwide, with most deaths occurring in developing countries (Health Effects Institute, 2019).

The recent development (e.g., Piedrahita et al., 2014) and application (e.g., Steinle et al., 2013; Cross et al., 2017; Rai et al., 2017; Feinberg et al., 2018; Hagan et al., 2018; Jiao et al., 2016; Mijling et al., 2018; Zimmerman et al., 2018; Malings et al., 2019; Ellenburg et al., 2019) of low-cost air pollution sensors has resulted in great interest in air pollution measurements using high density arrays and more recently in mobile monitoring from vehicles for high resolution mapping (Apte et al., 2017). Higher resolution data will allow better estimates of actual human exposure and provide the basis for policies that reduce the harmful effects of air pollutants on human health. This is particularly important from the environmental justice standpoint in that low-income families tend to live near air pollution sources. As a demonstration experiment, Google Street View cars were used to map the air pollutants $NO_2$, NO and black carbon within a ~25 $km^2$ area of Oakland, Calif. over a period of one year with 30-m resolution (Apte et al., 2017). Highly accurate, expensive instruments were used in that work, and those instruments were housed inside the vehicle with air sampling achieved using an inert inlet tube that had to pass through the body of the vehicle to the outside.

However, in order to scale to potentially hundreds of thousands of vehicles in thousands of cities throughout the world, less expensive sensor-based air quality measurements will be required, and it is desirable that the sensor package be mounted outside the vehicle (e.g., bus, tram, taxi, delivery vehicle) so as not to take up passenger or cargo space. Furthermore, the need to bring ambient sample air into the vehicle through a sampling line may require alteration of the vehicle, which would be relatively difficult and expensive to do on a large number of vehicles. For widespread use, the air quality sensor measurement package should be easy to attach and very importantly should not be affected by weather conditions such as rain, hail, sleet and high wind. Proceeding from this background, the following disclosure proposes a robust, weather-resistant mobile air monitoring platform that can be easily mounted to nearly any vehicle for high resolution mapping of various air characteristics and that is capable of making reliable air pollutant measurements when the vehicle is either moving or stationary.

The foregoing examples of the related art and limitations therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above described problems have been reduced or eliminated, while other embodiments are directed to other improvements.

The present disclosure relates to an enclosure or housing for one or more air monitoring devices that is readily mounted to the outside of a vehicle for measuring one or more characteristics of ambient air along the path of the vehicle. Such air monitoring devices include sensors and instruments (these terms are used interchangeably here) that provide a measurement of one or more air pollutant or meteorological variables, for example, the presence or concentration of gaseous, particulate and biological agents, and/or physical properties of the air such as temperature, pressure and humidity. The described enclosure allows sampling of ambient air without significant loss of gaseous or particulate pollutants, while protecting the measurement devices from inclement weather conditions such as wind, rain, snow, hail, sleet, etc.

The disclosed enclosure for an instrument package is mountable on the roof or other surface of the outside of a vehicle for the purpose of characterizing the composition or properties of ambient air. Due to the mobility of the vehicle, the system can be used to explore air pollution levels at various locations and thus for the production of highly resolved maps of air pollutants and other measured air properties. The enclosure design allows air measurements during high wind conditions, including both external winds and wind created by the movement of the vehicle itself, and during precipitation events such as rain, snow, sleet and hail. The design provides for an approximately constant air sampling rate independent of the motion of the vehicle and wind conditions. This is important because the vehicle may travel at varying speeds and may stop frequently. The high flush rate of the enclosure reduces temperature rise within the enclosure and assures that the sampled air will exchange rapidly, enabling the instruments to measure the changes that are occurring in the properties or composition of the ambient air. In some embodiments, the enclosure comprises an optional impaction region to remove large particles such as any residual mist, dust and pollen from the sampled air prior to entering the measurement chamber while providing a high transmission rate for gaseous species and smaller particulates (e.g., particulates with diameters <2.5 microns), thereby protecting the sensors/instruments from contamination.

Accordingly, one aspect of the present disclosure is a device and method for sampling ambient air for measurements of air composition and meteorological parameters on a moving platform, such as an automobile, truck, bus, tram, train, boat or the like. As used herein, the term vehicle includes any and all such moving platforms.

Another aspect is a device and method for sampling ambient air for measurements of air composition and meteorological parameters on such a moving platform in various weather conditions, including inclement weather such as precipitation events.

Another aspect is the sampling of ambient air into a measurement chamber mounted to the outside of a vehicle when the vehicle is either moving or stationary.

Another aspect is to provide a continuous supply of sample air across various moving speeds of the vehicle.

Another aspect is to provide a continuous supply of sample air under various weather conditions, including during a precipitation event.

Another aspect comprises the use of a multi-chamber design.

Another aspect is the use of a fan to force air from a partially open chamber into an inner chamber containing air measurement sensors.

Another aspect is the use of an impaction plate configuration to remove precipitation and other large particles from the sampled air.

In one embodiment, a mobile air monitoring enclosure device comprises a housing containing an inlet chamber region, an impaction chamber region, and a measurement chamber region. The inlet chamber region is in fluid communication with the impaction chamber region, and the impaction chamber region is in fluid communication with the measurement chamber region. The inlet chamber region has one or more airflow inlets which extend through a rear side of the housing to the outside environment. This is the housing side that is arranged opposite the forward travel direction of the vehicle. The measurement chamber region has one or more airflow outlets which extend through the housing to the outside environment. The device further comprises a fan configured to convey a sampling airflow through the housing. During use, at least a portion of the airflow enters the housing from the outside environment into the inlet chamber region, then flows into the impaction chamber region, then flows into the measurement chamber region, and then exits the housing to the outside environment from the measurement chamber region. The housing is preferably made of a lightweight plastic material and has an aerodynamic profile, at least with respect to the forward travel direction of the vehicle to which the device is mounted. For example, at least a front side of the housing (which is opposite the rear side of the housing containing the airflow inlet or inlets) may have an aerodynamic profile.

An air measurement instrument package is arranged in the measurement chamber region, wherein the air measurement instrument package is configured to measure one or more characteristics of the sampling airflow. For example, the package may comprise one or more instruments or sensors for detecting air pollutants and/or measuring concentrations of air pollutants. Additionally or alternatively, the package may comprise one or more instruments or sensors for measuring temperature, pressure and/or humidity data. Preferably, the air measurement instrument package is mounted on standoffs which elevate the air measurement instrument package off a floor of the housing within the measurement chamber region.

If included in the design, the impaction chamber region preferably comprises one or more baffles which define a non-linear path of the sampling airflow through the impaction chamber region. During use, water droplets and other larger particles will collect on the baffles, while smaller particles are able to pass through the tortuous flow path of the impaction chamber region into the measurement chamber region. For example, these baffle structures may be provided as one or more walls or plates which extend across a portion of the height of the impaction chamber region.

The device may also have one or more drainage ports which extend through a bottom side of the housing, for example to the outside environment or a drainage collection component. The drainage ports help prevent liquid from accumulating within the housing. The drainage ports may be provided within the inlet chamber region, impaction chamber region and/or measurement chamber region depending on the arrangement. If provided in the measurement chamber region, the one or more airflow outlets and drainage ports may be provided by the same opening(s). The one or more outlet openings in the measurement chamber region should have a higher fluid conductance than the combined fluid conductance of the one or more drainage ports of the other chamber regions, in order to ensure sufficient airflow reaches the air measurement instrument package.

Preferably, the one or more airflow inlets of the inlet chamber region have louvers, which extend outward from the rear side of housing at a downward angle. These louvers help reduce ingress of rain and other precipitation from entering the enclosure. Likewise, the one or more drainage ports will also preferably have louvers, which extend outward from the bottom side of the housing at an angle in the direction of the rear side of the housing. In this way, these louvers help prevent ingress of precipitation up into the housing when the vehicle is in motion.

The fan may be arranged: between the inlet chamber region and the impaction chamber region inside the housing; between the impaction chamber region and the measurement chamber region inside the housing; between the inlet chamber region and the measurement chamber region inside the housing (in embodiments without an impaction chamber region); at an airflow outlet of the one or more airflow outlets in the measurement chamber region; or at an airflow inlet of the one or more airflow inlets in the inlet chamber region.

Accordingly, a system for mobile air monitoring of an outside environment comprises an enclosure device according to present disclosure and a vehicle, with the device mounted to an exterior surface of the vehicle, wherein the rear side of the housing, through which the one or more airflow inlets extend from the outside environment into the inlet chamber, is arranged opposite a forward direction of travel of the vehicle.

In one embodiment, a method for mobile air monitoring of an outside environment using a device mounted to an exterior of a vehicle comprises: drawing an airflow from the outside environment into an inlet chamber region provided within a housing of the device, wherein the inlet chamber region comprises one or more airflow inlets which extend through a rear side of the housing to the outside environment; conveying the airflow from the inlet chamber region into an impaction chamber region provided within the housing of the device, wherein the impaction chamber region comprises one or more baffles defining a non-linear path for the airflow through the impaction chamber region; conveying the airflow from the impaction chamber region into a measurement chamber region provided within the housing of the device, wherein the measurement chamber region contains an air measurement instrument package comprising one or more instruments; measuring one or more characteristics of the airflow using the measurement instrument package; and conveying the airflow from the measurement chamber region into the outside environment, wherein the measurement chamber region comprises one or more airflow outlets which extend through the housing to the outside environment. By translocating the vehicle, the method can be used to map measurements of the one or more characteristics of the airflow at different locations. Further, these characteristics can be continuously measured during transit, such that high-resolution mapping is possible. The method is also not limited by the type of vehicle, since the device can be mounted across a wide variety of vehicles (e.g. automobiles such as cars and trucks, buses, trams, trains, watercraft, etc.). As before, the rear side of the housing preferably faces opposite a forward direction of travel of the vehicle. If the device includes an impaction chamber region, the method may further comprise draining moisture and larger particles which accumulate on the one or more baffles of the impaction chamber through one or more drainage ports which extend through the bottom side of the housing. With this method and design, the flow rate of the airflow through the housing device can be provided independent of the motion of the vehicle, meaning measurements can be taken regardless of whether the vehicle is stationary or moving.

In addition to the exemplary aspects and embodiments described above, further aspects and embodiments will become apparent by reference to the accompanying drawings forming a part of this specification wherein like reference characters designate corresponding elements or structures in the several views.

Before further explaining the depicted embodiments, it is to be understood that the invention is not limited in its application to the details of the particular arrangements shown, since the invention is capable of other embodiments. It is intended that the embodiments and figures disclosed herein are to be considered illustrative rather than limiting. Also, the terminology used herein is for the purposes of description and not limitation.

DETAILED DESCRIPTION

Figure 1:
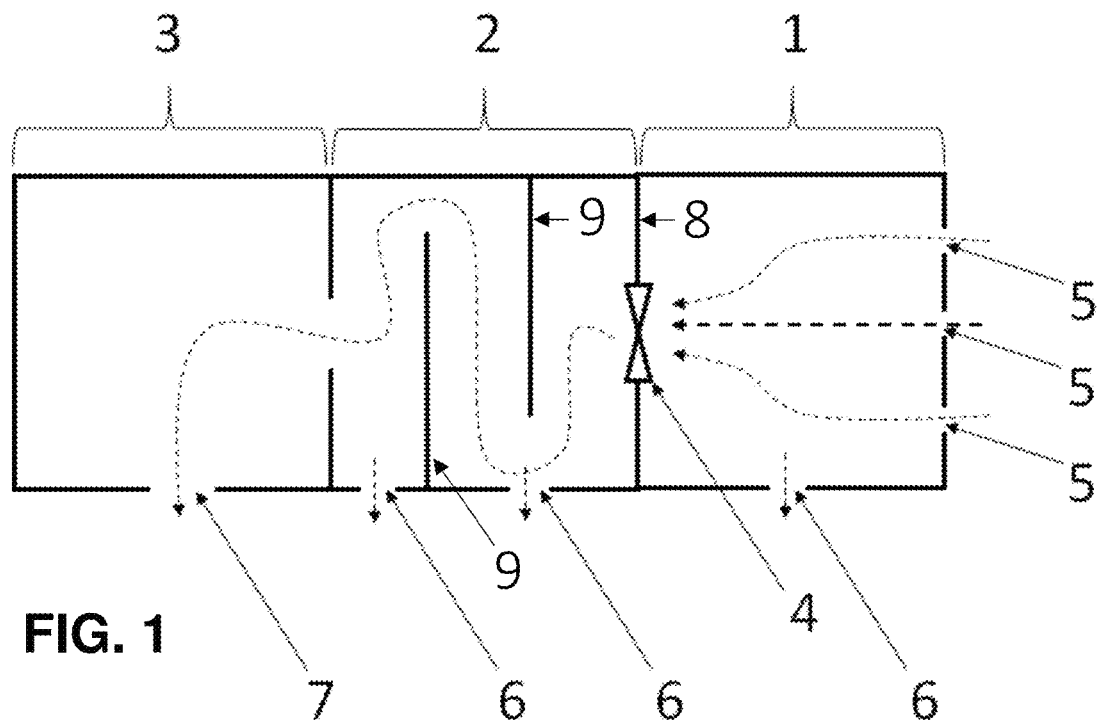
FIG. 1 shows a schematic diagram, from a sectional side view, of an air monitoring enclosure for mounting on the roof or other surface of the outside of a vehicle.

One possible embodiment of an enclosure or housing according to the present disclosure is depicted in FIG. 1. The enclosure is divided into three chambers or regions 1, 2, 3. Chamber 1 is provided opposite the front of the vehicle (opposite the forward direction of travel of the vehicle). Chamber region 1 may be substantially enclosed from the outside in order to reduce infiltration of excess water or other debris in sampling the air. Optional chamber region 2 is provided between chamber region 1 and chamber region 3 with respect to the flow of sample air through the enclosure. Chamber region 3 contains one or more air measurement devices—collectively an instrument or sensor package. During operation, air is drawn through inlets 5 into the rear chamber region 1 by fan 4, forced through optional chamber region 2, which contains a tortuous path for impaction of large particles, and enters chamber region 3. In the depicted design, the fan 4 is arranged in a wall 8 separating the inlet chamber region 1 from the impaction chamber region 2 in the path of the airflow. In other designs, fan 4 may be arranged between the impaction chamber region 2 and the measurement chamber region 3, or as an exit fan in the measurement chamber 3 that expels air and thereby draws air into the device upstream, or as an entry fan at the inlet chamber region 1 that pushes air into the device. Providing the fan 4 as an exit fan can be advantageous in reducing potential interference between the fan and the sample air being measured (e.g. particle accumulation on the fan). Sample air is expelled through drainage ports or outlets 6 provided along the bottom of the enclosure, which also drain any liquid water that inadvertently enters the enclosure. Optional chamber region 2 comprises an impactor wall, plate or baffle configuration 9 for removal of fugitive rain droplets, sleet, snow and other large particles such as dust and pollen. This chamber region 2 provides a tortuous path through which air, gaseous air pollutants and small particles having diameters of ~2.5 μm and smaller pass with high efficiency. The baffles 9 here are provided as vertical walls which extend across a portion of the height of the impaction chamber 2 to define a non-linear path of the airflow through this region 2. In other designs, the baffles 9 extend at an angle to the vertical. A wide variety of design configurations are possible for the baffle structures. The fan 4 imparts sufficient momentum to larger particles such as rain droplets (~500 to 4,000 μm) which then cannot make all of the turns through the tortuous path of impactor chamber region 2, and thus collide with a baffle wall 9 where they coalesce with other droplets and flow via gravity to the chamber floor where they exit via drainage ports 6. The pressurization of chambers 2 and 3 by the fan 4 facilitates liquid water removal, with a small fraction of the air sampled by the fan exiting each of the drainage ports 6 as well. The dashed arrows illustrate the flow of air drawn from outside the enclosure by fan 4 into chamber 1, through the tortuous path of optional impactor chamber 2, into the measurement chamber 3, and exiting through outlet 7, which has higher conductance than the combination of drainage ports 6.

Chamber region 2 may be omitted in embodiments where larger particles do not interfere with the measurements or instruments, or where such larger particles are desired for the measurements. In such configurations, the inlet and measurement chamber regions 1, 3 may effectively merge into same chamber region, with the instrument package arranged between the one or more inlets 5 and the one or more outlets 7, particularly where the fan 4 is not provided along the path of the airflow between the chamber regions 1 and 3, for example, where the fan 4 is arranged at outlet 7. Otherwise, it is will be generally preferable to include the impaction chamber region 2 with one or more baffle structures 9, which define a non-linear path of the sampling airflow, in order to filter out such particles and moisture. It should be appreciated that the configuration of the impaction walls, plates or baffles 9 in chamber region 2 may be selected according to the requirements of the particular application.

Figure 2:
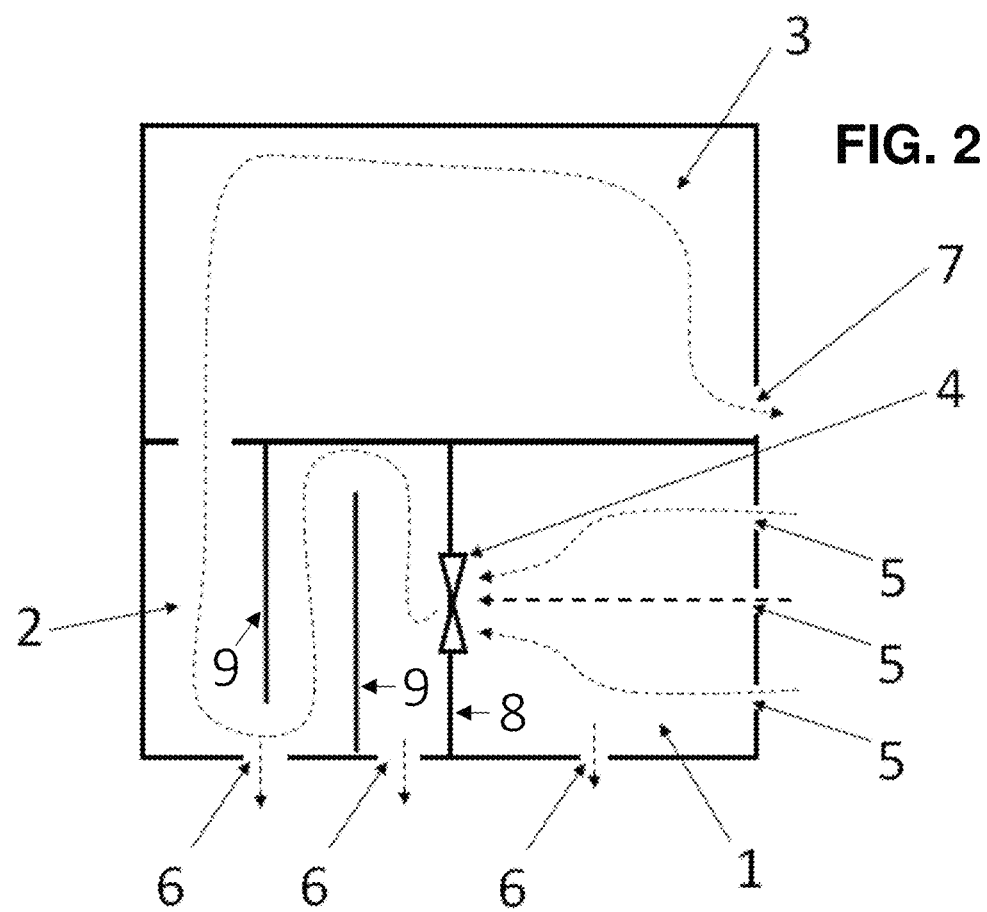
FIG. 2 shows a schematic diagram, from a sectional side view, of an alternative air monitoring enclosure with a stacked configuration.

The embodiment of FIG. 2 comprises an alternative stacked arrangement of the three regions or chambers 1, 2, 3. Descriptions regarding the previous embodiment otherwise apply equally to this embodiment, and vice versa. Again, ambient air is drawn through inlets 5 into the covered chamber region 1 by fan 4, and conveyed into the impaction zone 2 for removal of fugitive rain drops and other particles, and then enters chamber region 3 containing the sensor package. Drain holes 6 allow liquid water to be removed. The pressurization of chambers 2 and 3 by the fan 4 (also dependent on size of drain holes 6) facilitates water removal, with a small fraction of the air sampled by the fan 4 exiting drains 6 as well. The dashed arrows illustrate the flow of air drawn by fan 4 into chamber 1, through the tortuous path of the impactor 2 and into the measurement chamber 3. Other arrangements of the three chambers are possible as well. For example, chamber 3 could lie below chambers 1 and 2 (or chambers 1 and 2 could be located above chamber 3), the only requirement being that the order of flow be chamber 1 followed by chamber 2 followed by chamber 3. Also, the fan 4 could be located between chambers 2 and 3 rather than chambers 1 and 2 or located at the exit opening 7. One skilled in the art would be able to design other arrangements of the three chamber regions, inlets/outlets, and fan to accomplish the same result, which is to sample air through a covered chamber region, pass the air through an optional impaction region, pass the sample air through the chamber region containing the air measurement instruments, and exit the enclosure.

Figure 3:
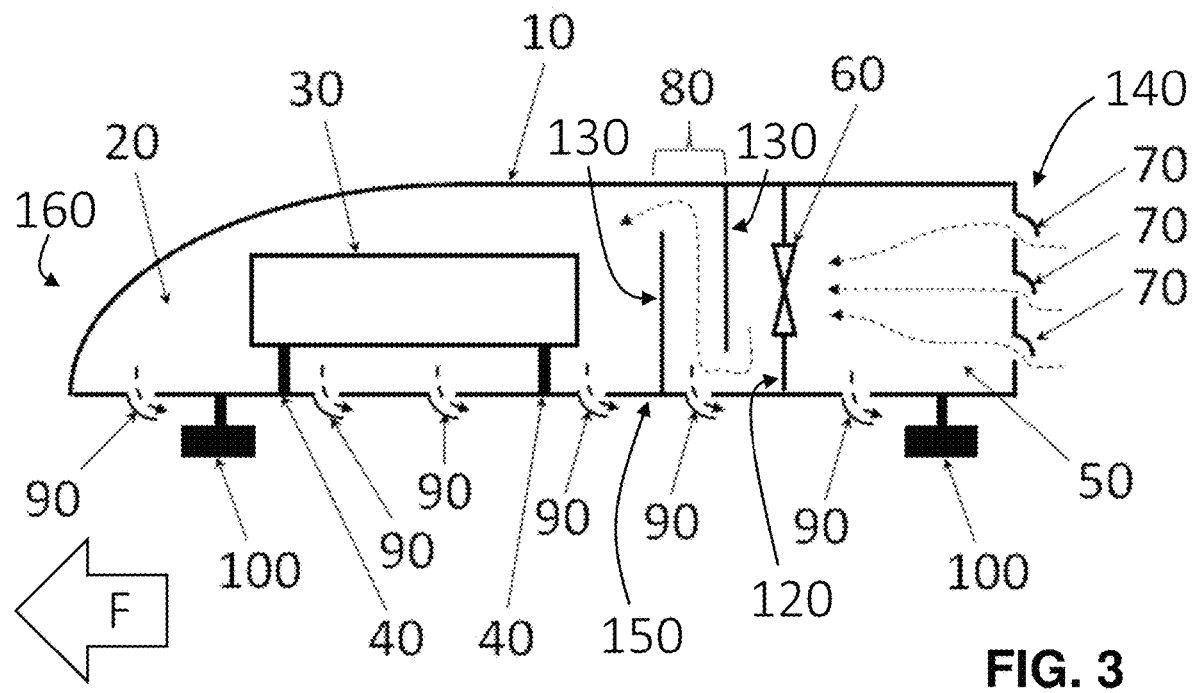
FIG. 3 shows a schematic diagram, from a sectional side view, of an embodiment of an air monitoring enclosure device incorporating the design of FIG. 1.

FIG. 3 shows an embodiment of an air sampling enclosure device according to the design of FIG. 1 in more detail in order to illustrate other features. An outer cover or shell 10 is preferably made of a lightweight plastic material, preferably white in color to absorb as little sunlight as possible, and preferably having an aerodynamic design so as the create as little aerodynamic resistance as possible. The housing 10 contains a measurement chamber region 20 that houses an air measurement instrument package 30. Here, the measurement chamber region 20 is located on the front side 160 of the housing 10. The rear side 140 of the housing 10 is opposite the front side 160, and therefore arranged opposite the forward direction of travel of the vehicle (indicated by the arrow F). A bottom side 150 of the housing 10 faces the vehicle surface. The instrument package 30 is offset from the floor of the housing 10 by standoffs 40 in order to prevent any water or other liquid that accumulates in chamber region 20 from contacting the instrument package 30. Sample air is drawn into covered chamber region 50 by fan 60 and is forced through impaction region or chamber 80 prior to entering the sample chamber region 20. Here, the fan 60 is arranged between the inlet chamber region 50 and the impaction chamber region 80. In particular, the fan 60 is provided in the wall 120 that separates chamber regions 50, 80 and therefore in the path of the airflow. As mentioned above, other locations of the fan 60 are also possible. The sample air exits through one or more (six shown here) air outlets 90 that also serve as liquid water drains. These openings 90 extend through the bottom side 150 of the housing 10.

The housing 10 has typically two or more (two shown in this cross-sectional diagram) vehicle mounting structures 100; although designs with a single mounting structure are also possible. Here, the mounting feet 100 extend downward from the bottom side 140 of the housing 10 to attach the device to an exterior surface of the vehicle. The device is preferably mounted on a horizontal or substantially horizontal surface of the vehicle for better stability and drainage, but may be mounted on other non-horizontal vehicle surfaces as well with modification to the enclosure and mounting mechanism design. The mounting feet 100 preferably contain magnets for vehicles having steel bodies or suction cups for vehicles having non-ferrous bodies. Additional mounting straps (not shown) may also be desirable for use as the primary means of securement to a vehicle roof or other surface or as a secondary means when magnetic or suction cup attachments are used. The use of mounting straps, suction cups, and magnetic mounts is well known and such devices are available commercially for attachment of luggage racks, ski racks, bicycle racks, etc. to vehicle bodies. Further illustration of the mounting of the device to the vehicle is therefore not necessary for the understanding of those skilled in the art.

In this depicted design, the one or more airflow inlet openings of the inlet chamber region 50 comprise louvers 70. Louvres 70 are preferable to simple holes or slits to provide an air entrance to chamber region 50 in order to minimize the amount of rain and other precipitation from entering the enclosure. The louvres 70 extend outward from the rear side 140 of the housing 10 at a downward angle. Similarly, louvres 90, oriented as shown in FIG. 3 facing backward away from the forward direct of travel F of the vehicle, are desirable to prevent air from forcing precipitation into the various chambers of the enclosure when the vehicle is in motion. The louvres 90 extend outward from the bottom side 150 of the housing 10 at an angle in the direction of the rear side 140 of the housing 10.

Figure 4:
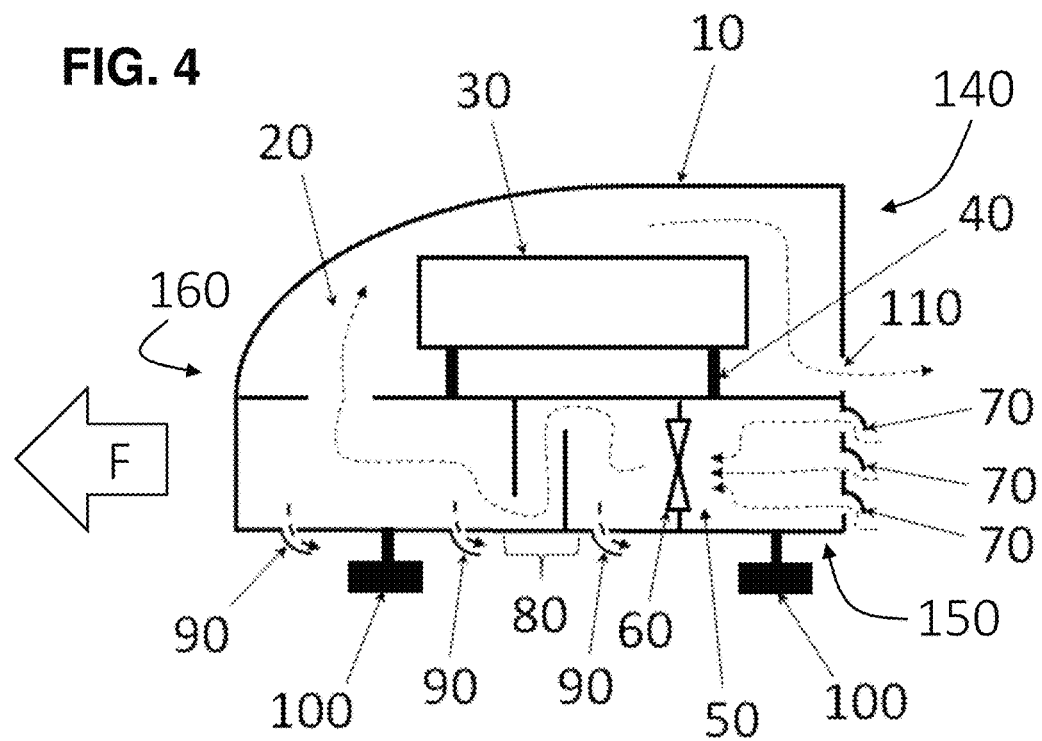
FIG. 4 shows a schematic diagram, from a sectional side view, of an embodiment of an air monitoring enclosure device incorporating the design of FIG. 2.

FIG. 4 shows an embodiment of mobile air enclosure device according the design of FIG. 2. The labeled elements have the same meaning as in FIG. 3. The previous descriptions apply equally here. This embodiment illustrates one of several alternatives for rearranging the basic elements of the disclosed air sampling package, the requirements being an entry chamber region 50 with one or more inlets 70, a fan 60, an optional impaction chamber region 80, and a chamber region 20 that contains the instrument package 30 and one or more outlets 110 (exit 110 corresponds to the openings 90 in the measurement chamber 20 of FIG. 3).

While a number of aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations, which are within their true spirit and scope. Each embodiment described herein has numerous equivalents.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure. When a Markush group or other grouping is used herein, all individual members of the group and all combinations and sub-combinations possible of the group are intended to be individually included in the disclosure.

In general, the terms and phrases used herein have their art-recognized meaning, which can be found by reference to standard texts, journal references and contexts known to those skilled in the art. The above definitions are provided to clarify their specific use in the context of the invention.

CITED LITERATURE

American Lung Association (2019) *State of the Air* 2019.

Apte, J. S., Messier, K. P., Gani, S., Brauer, M., Kirchstetter, T. W., Lunden, M. M., Marshall, J. D., Portier, C. J., Vermeulen, R. C. H. and Hamburg, S. P. (2017) High-resolution air pollution mapping with Google Street View cars: Exploiting big data, *Environmental Science & Technology*, 51, 6999-7008.

Cross, E. S., Williams, L. R., Lewis, D. K., Magoon, G. R., Onasch, T. B., Kaminsky, M. L., Worsnop, D. R. and Jayne, J. T. (2017) Use of electrochemical sensors for measurement of air pollution: Correcting interference response and validating measurements, *Atmospheric Measurement Techniques*, 10, 3575-3588.

Ellenburg, J. A., Williford, C. J., Rodriguez, S. L., Andersen, P. C., Turnipseed, A. A., Ennis, C. A., Basman, K. A., Hatz, J. M., Prince, J. C., Meyers, D. H., Kopala, D. J., Samon, M. J., Jaspers, K. J., Lanham, B. J., Carpenter, B. J. and Birks, J. W. (2019) Global Ozone (GO3) Project and AQTreks: Use of evolving technologies by students and citizen scientists to monitor air pollutants, *Atmospheric Environment*, in press.

Feinberg, S., Williams, R., Hagler, G. S. W., Rickard, J., Brown, R., Garver, D., Harshfield, G., Stauffer, P., Mattson, E., Judge, R. and Garvey, S. (2018) Long-term evaluation of air sensor technology under ambient conditions in Denver, Colo., *Atmospheric Measurement Techniques*, 11, 4605-4615.

Hagan, D. H., Isaacman-VanWertz, G., Franklin, J. P., Wallace, L. M. M., Kocar, B. D., Heald, C. L. and Kroll, J. H. (2018) Calibration and assessment of electrochemical air quality sensors by co-location with regulatory-grade instruments, *Atmospheric Measurement Techniques*, 11, 315-328.

Health Effects Institute (2019) *State of Global Air* 2019.

Jiao, W., Hagler, G., Williams, R., Sharpe, R., Brown, R., Garver, D., Judge, R., Caudill, M., Rickard, J., Davis, M., Weinstock, L., Zimmer-Dauphinee, S. and Buckley, K. (2016) Community Air Sensor Network (CAIRSENSE) project: Evaluation of low-cost sensor performance in a suburban environment in the southeastern United States, *Atmospheric Measurement Techniques*, 9, 5281-5292.

Malings, C., Tanzer, R., Hauryliuk, A., Saha, P. K., Robinson, A. L., Presto, A. A. and Subramanian, R. (2019) Fine particle mass monitoring with low-cost sensors: Corrections and long-term performance evaluation, *Earth and Space Science Open Archive*, DOI: 10.1080/02786826.2019.1623863

Mijling, B., Jiang, Q., de Jonge, D. and Bocconi, S. (2018) Field calibration of electrochemical $NO_2$ sensors in a citizen science context, *Atmospheric Measurement Techniques*, 11, 1297-1312.

Piedrahita, R., Xiang, Y., Masson, N., Ortega, J., Collier, A., Jiang, Y., Li, K., Dick, R. P., Lv, Q., Hannigan, M. and Shang, L. (2014) The next generation of low-cost personal air quality sensors for quantitative exposure monitoring, *Atmospheric Measurement Techniques*, 7, 3325-3336.

Rai, A. C., Kumar, P., Pilla, F., Skouloudis, A. N., Di Sabatino, S., Ratti, C., Yasaar, A and Rickerby, D. (2017) End-user perspective of low-cost sensors for outdoor air pollution monitoring, *Science of The Total Environment*, 573, 607-608:691-705.

Steinle, S., Reis, S. and Sabel, C. E. (2013) Quantifying human exposure to air pollution—Moving from static monitoring to spatio-temporally resolved personal exposure measurement, *Science of the Total Environment*, 443, 184-193.

Zimmerman, N., Presto, A. A., Kumar, S. P. N., Gu, J., Hauryliuk, A., Robinson, E. S., Robinson, A. L. and Subramanian, R. (2018) A machine learning calibration model using random forests to improve sensor performance for lower-cost air quality monitoring, *Atmospheric Measurement Techniques*, 11, 291-313.

The invention claimed is:

1. A device configured to be mounted to an exterior of a vehicle for mobile air monitoring of an outside environment, comprising:
    a housing containing an inlet chamber region, an impaction chamber region, and a measurement chamber region, wherein the inlet chamber region is in fluid communication with the impaction chamber region, and the impaction chamber region is in fluid communication with the measurement chamber region;
    a fan configured to convey a sampling airflow through the housing, wherein at least a portion of the sampling airflow enters the housing from the outside environment into the inlet chamber region, then flows into the impaction chamber region, then flows into the measurement chamber region, and then exits the housing to the outside environment from the measurement chamber region;
    an air measurement instrument package arranged in the measurement chamber region, wherein the air measurement instrument package is configured to measure one or more characteristics of the sampling airflow; and
    one or more drainage ports which extend through a bottom side of the housing;
    wherein the inlet chamber region comprises one or more airflow inlets which extend through a rear side of the housing to the outside environment;
    wherein the impaction chamber region comprises one or more baffles which define a non-linear path of the sampling airflow through the impaction chamber region;
    wherein the measurement chamber region comprises one or more airflow outlets which extend through the housing to the outside environment.

2. The device of claim 1, wherein the housing is made of a plastic material.

3. The device of claim 1, wherein at least a front side of the housing has an aerodynamic profile, the front side of the housing being opposite the rear side of the housing.

4. The device of claim 1, further comprising mounting feet which extend downward from the bottom side of the housing for mounting the device to an exterior surface of the vehicle.

5. The device of claim 1, wherein the rear side of the housing, through which the one or more airflow inlets extend from the outside environment into the inlet chamber region, is arranged opposite a forward direction of travel of the vehicle when the device is mounted to the vehicle.

6. The device of claim 1, wherein the one or more baffles of the impaction chamber region are provided as one or more walls or plates which extend across a portion of the height of the impaction chamber region.

7. The device of claim 1, wherein the one or more airflow inlets of the inlet chamber region have louvers, which extend outward from the rear side of housing at a downward angle.

8. The device of claim 1, wherein the one or more drainage ports have louvers, which extend outward from the bottom side of the housing at an angle in a direction of the rear side of the housing.

9. The device of claim 1, wherein at least one drainage port of the one or more drainage ports extend through the bottom side of the housing into the inlet chamber region.

10. The device of claim 1, wherein at least one drainage port of the one or more drainage ports extend through the bottom side of the housing into the impaction chamber region.

11. The device of claim 1, wherein at least one drainage port of the one or more drainage ports extend through the bottom side of the housing into the measurement chamber region.

12. The device of claim 11, wherein the one or more airflow outlets of the measurement chamber region and the at least one drainage port of the measurement chamber region are provided by the same opening(s).

13. The device of claim 1, wherein the air measurement instrument package is mounted on standoffs which elevate the air measurement instrument package off a floor of the housing within the measurement chamber region.

14. The device of claim 1, wherein the air measurement instrument package comprises one or more instruments for detecting air pollutants and/or measuring concentrations of air pollutants.

15. The device of claim 1, wherein the air measurement instrument package comprises one or more instruments for measuring temperature, pressure and/or humidity data.

16. The device of claim 1, wherein the fan is arranged between the inlet chamber region and the impaction chamber region inside the housing.

17. The device of claim 1, wherein the fan is arranged at an airflow outlet of the one or more airflow outlets, which airflow outlet extends through the housing to the outside environment, in the measurement chamber region.

18. The device of claim 1, wherein the impaction chamber region is arranged horizontally adjacent to the inlet chamber region opposite the rear side of the housing, and the measurement chamber region is arranged above both the inlet chamber region and the impaction chamber region.

19. The device of claim 1, wherein the impaction chamber region is arranged horizontally adjacent to the inlet chamber region opposite the rear side of the housing, and the measurement chamber region is arranged horizontally adjacent to the impaction chamber region opposite the inlet chamber region.

20. The device of claim 1, wherein the one or more airflow outlets of the measurement chamber region have a higher fluid conductance than the one or more drainage ports.

21. A system for mobile air monitoring of an outside environment comprising a vehicle and a device according to claim 1, the device mounted to an exterior surface of the vehicle, wherein the rear side of the housing, through which the one or more airflow inlets extend from the outside environment into the inlet chamber region, is arranged opposite a forward direction of travel of the vehicle.

* * * * *